United States Patent
Okada et al.

(10) Patent No.: US 9,433,533 B2
(45) Date of Patent: Sep. 6, 2016

(54) PATCH PACKAGE STRUCTURE

(75) Inventors: Katsuhiro Okada, Ibaraki (JP); Yoshihiro Iwao, Ibaraki (JP); Kensuke Matsuoka, Ibaraki (JP)

(73) Assignee: NITTO DENKO CORPORATION, Tokyo (JP)

( * ) Notice: Subject to any disclaimer, the term of this patent is extended or adjusted under 35 U.S.C. 154(b) by 764 days.

(21) Appl. No.: 11/972,910

(22) Filed: Jan. 11, 2008

(65) Prior Publication Data

US 2008/0172015 A1   Jul. 17, 2008

(30) Foreign Application Priority Data

Jan. 11, 2007 (JP) .................................. 2007-003313

(51) Int. Cl.
*A61M 35/00* (2006.01)
*A61F 13/02* (2006.01)
(Continued)

(52) U.S. Cl.
CPC .......... *A61F 13/0203* (2013.01); *A61F 13/551* (2013.01); *A61F 15/001* (2013.01)

(58) Field of Classification Search
CPC ...... A61M 35/00; A61F 13/00; A61F 13/02; A61B 17/06; A61B 19/02; A61L 15/00
USPC .................. 604/289, 304, 307, 308
See application file for complete search history.

(56) References Cited

U.S. PATENT DOCUMENTS 4,176,664 A * 12/1979 Kalish ........................... 604/307
4,182,449 A   1/1980 Kozlow
(Continued)

FOREIGN PATENT DOCUMENTS

EP   0423374 A1   4/1991
EP   1688123 A1   8/2006
(Continued)

OTHER PUBLICATIONS

European Office Action dated Dec. 18, 2009 in Application No. 08000374.2-2320.
(Continued)

*Primary Examiner* — Tatyana Zalukaeva
*Assistant Examiner* — Ilya Treyger
(74) *Attorney, Agent, or Firm* — Sughrue Mion, PLLC (57) ABSTRACT

The present invention provides a patch package structure, which includes: a package including a first sheet material which is planar and a second sheet material which has been molded, the first and second sheet materials being sealed together in peripheral parts thereof, and a patch disposed in the package, in which the patch contains a backing, a pressure-sensitive adhesive layer laminated on at least one side of the backing, and a release liner which protects a pressure-sensitive adhesive surface of the pressure-sensitive adhesive layer; the second sheet material has been molded so as to have a protrudent part in at least a substantially central area thereof, the protrudent part having a planar outer shape larger than a planar outer shape of the release liner and having at least one recessed part; d is not smaller than T, in which d is the minimum gap distance between the inner surface of the first sheet material and the inner surface of the second sheet material at the recessed part and T is a thickness of the patch; and, at the boundary between the sealed part where the first and second sheet materials are sealed together and an unsealed part, the outer surface of the second sheet material rises at an obtuse angle.

7 Claims, 5 Drawing Sheets (51) Int. Cl.
*A61F 13/551* (2006.01)
*A61F 15/00* (2006.01)
*A61F 13/00* (2006.01)
*A61B 17/06* (2006.01)

(56) References Cited

U.S. PATENT DOCUMENTS

| | | | |
|---|---|---|---|
| 4,880,416 A * | 11/1989 | Horiuchi et al. | 424/448 |
| 5,505,306 A | 4/1996 | Akemi et al. | |
| 5,656,282 A * | 8/1997 | Cook | A01N 25/18 424/408 |
| 5,698,217 A | 12/1997 | Wilking | |
| 5,950,830 A * | 9/1999 | Trigger | 206/440 |
| 6,991,095 B1 * | 1/2006 | Yamasoto et al. | 206/204 |
| 2007/0144928 A1 | 6/2007 | Higo et al. | |

FOREIGN PATENT DOCUMENTS

| | | |
|---|---|---|
| JP | 4-51782 Y2 | 12/1992 |
| JP | 10-511330 A | 11/1998 |
| JP | 2000-070330 A | 3/2000 |
| WO | 96/19394 A1 | 6/1996 |
| WO | 2005048910 A1 | 6/2005 |
| WO | 2005-072716 A1 | 8/2005 |

OTHER PUBLICATIONS

Communication dated Jun. 11, 2012 issued by the European Patent Office in corresponding European Application No. 08 000 374.2.
Summons to attend oral proceedings dated Jan. 24, 2012 from the European Patent Office in counterpart European application No. 08000374.2.
Office Action dated Jan. 24, 2012 from the State Intellectual Property Office of the People's Republic of China in counterpart Chinese application No. 200810002888.7.
CBDL Patentanwalte (Opposition against EP 1944001). "Written submissions (R. 116 EPC) and further prior art." Mar. 7, 2012.
Office Action dated Jun. 12, 2012 issued by the Japanese Patent Office in counterpart Japanese Application No. 2007-334141.
Office Action dated Jul. 18, 2012, issued by The State Intellectual Property Office of the People's Republic of China in counterpart Application No. 200810002888.7.
Brief Communication dated Sep. 13, 2010 issued in corresponding European application No. 08000374.2.
Office Action dated Oct. 19, 2010, issued in corresponding Canadian application No. 2,617,455.

* cited by examiner

PATCH PACKAGE STRUCTURE

FIELD OF THE INVENTION

The present invention relates to a patch package structure which includes: a package including a first sheet material which is planar and a second sheet material which has been molded, the first and second sheet materials being sealed together in peripheral parts thereof; and a patch disposed in the package.

BACKGROUND OF THE INVENTION

Patches to be applied to the skin for the purpose of, e.g., protecting the affected part and adhesive preparations to be applied to a surface of the skin of a mammal for the purpose of percutaneously administering a drug to the mammal have hitherto been developed. Recently, soft pressure-sensitive adhesive layers such as those holding a large amount of a liquid component therein tend to be employed for the purpose of obtaining a soft wear feeling during wear of the patch or reducing the skin irritation caused by separation of the horny layer upon stripping of the patch. With regard to adhesive preparations in which the pressure-sensitive adhesive layer contains a drug, a pressure-sensitive adhesive layer having a larger thickness is frequently employed in recent adhesive preparations so that the pressure-sensitive adhesive layer holds a large amount of a drug. In such a case, there may arise a trouble that the pressure-sensitive adhesive layer protrudes from an edge of the patch during storage and adheres to the inner surfaces of the package, whereby it becomes difficult to take out the patch out of the package. This tendency is significant when the pressure-sensitive adhesive layer is thick, since the amount of the pressure-sensitive adhesive layer is large.

Figure 8:
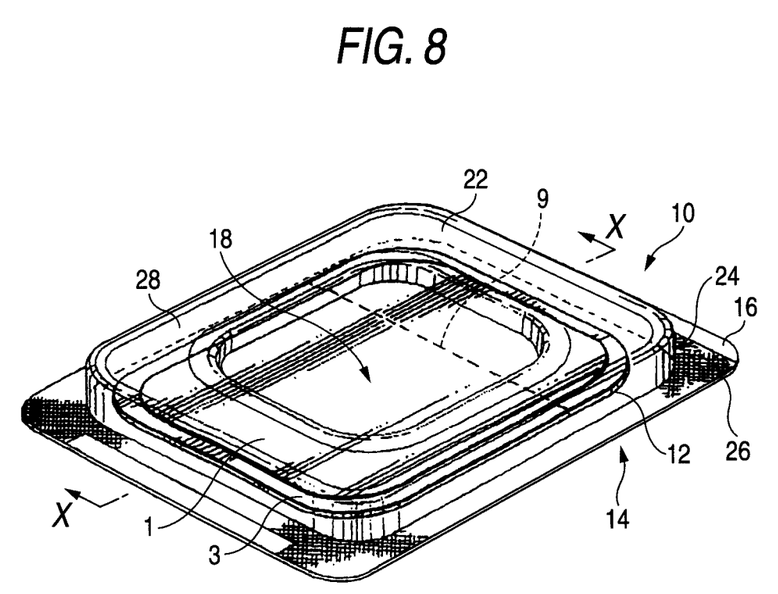
FIG. 8 is a slant view of a conventional patch package structure.

Various proposals have been made in order to overcome those problems. For example, JP-T-10-511330 (herein, the term "JP-T" as used herein means a published Japanese translation of a PCT patent application) discloses a package for disposing therein a patch to be applied to the skin (in this document, the structure composed of a pressure-sensitive adhesive layer and a backing excluding a release liner is referred to as "patch"). An example of this package is shown in FIG. 8.

This package is constituted of a blister pack 12 in a container form and a cap 14 in a sheet form, and a patch 1 is disposed in this package. In this package, the blister pack 12 in a container form has a central part 18 which is almost flat and horizontal and a peripheral outer part 22 which is deeper than the central part. The patch 1 has been attached to a release liner 3 larger than the patch. Owing to such a shape of the blister pack and the large release liner, peripheral parts of the patch 1 do not come into contact with any part of the package. There is a statement therein to the effect that the pressure-sensitive adhesive can be thus prevented from leaking out through the peripheral parts or lower side (release liner side) of the patch 1 and thereby bonding the patch 1 to the package.

However, since the blister pack 12 of this package is in the form of a container, the package as a whole becomes thick. Accordingly, the overall volume of this package becomes far larger than the patch itself. Consequently, this package is not fully satisfactory from the standpoints of the production cost thereof and the cost of handling including the transportation of packaged products.

An Example given in that document teaches that the constitution including an outer wall 24 having a substantially vertical upper region and the like enhance the overall strength of the package 10. However, the package described in this Example is thick as a whole as well as the angle formed by the outer wall 24 and the flange 26 in the blister pack (rising angle) is almost an right angle. Therefore, this package has such a drawback that, when the package is opened by cutting from the sealed part to the blister pack with scissors, a considerable power is necessary for the scissoring and, as a result, there is a possibility that the patch placed therein might be accidentally cut together with the package or, in the worst case, the scissors might injure the hand.

Furthermore, a laminated packaging material obtained by laminating sheet materials may be used as the material of the blister pack. In this case, there is a possibility that, when a blister pack having such a substantially right-angled bent part is molded from the sheet-form laminate packaging material, the blister pack thus obtained might suffer laminate failures such as delamination at the bent part. Especially in the case of a packaging material including an aluminum foil, there is a possibility that the aluminum foil might crack or otherwise break. In such a case, there is a possibility that the package structure might be impaired in impermeability to the package contents such as a drug, or in impermeability to light rays or gases, resulting in impaired quality stability of the package contents.

In this document, there is a statement to the effect that the depth (gap distance) of the central part of the blister pack from the cap is sufficiently larger than the total thickness of the patch and the release liner so that the patch and the release liner can move freely, whereby the patch is prevented from being pressed and the pressure-sensitive adhesive is hence prevented from being squeezed out from the downside of the patch (on the release liner side). There also is a statement to the effect that the outer part of the blister pack should also have a sufficient depth in order to prevent the pressure-sensitive adhesive from leaking out through edges of the patch and then coming into contact with the bottom of the blister pack. As described above, this document does not suggest a thin package structure.

Figure 9:
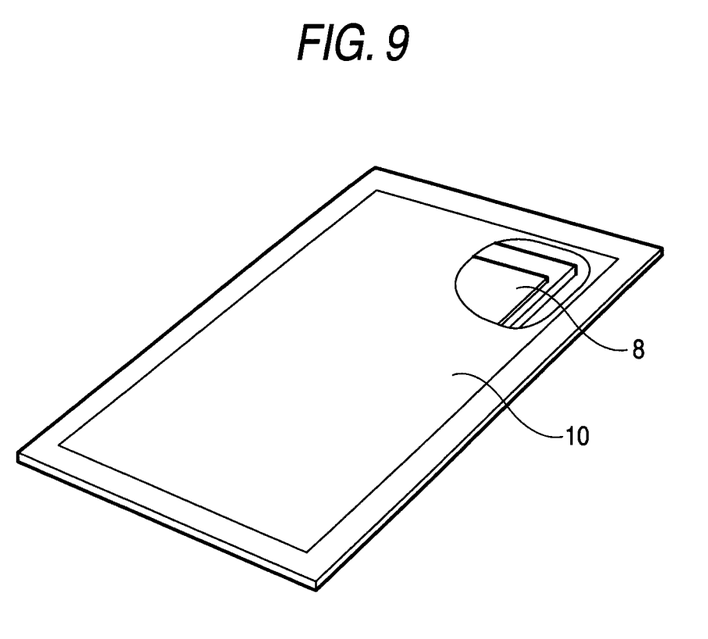
FIG. 9 is a slant view of another conventional patch package structure.

On the other hand, a patch package structure obtained without using a so-called blister pack has been conventionally utilized. It is produced by sandwiching a patch between two pieces of flexible sheet-form packaging materials having a slightly larger planar outer shape than the patch and then sealing the two pieces of flexible sheet-form packaging materials together in peripheral parts thereof. For example, JP-UM-B-4-51782 discloses a bag container obtained by sealing two pieces of planar sheet materials together in peripheral parts thereof, and an example of the bag container is shown in FIG. 9. However, since such a bag container is constituted of two pieces of planar flexible sheet materials, it has the following drawback. Namely, since a load is apt to be imposed on the patch in the thickness direction therefor and the patch freely moves in the bag container, the pressure-sensitive adhesive layer protruded from peripheral parts of the patch comes into contact with the inner surfaces of the bag container and the components of the pressure-sensitive adhesive layer thus adhere to the inner surfaces of the bag container, whereby it often becomes difficult to take out the patch out of the bag container. This tendency is significant especially when the pressure-sensitive adhesive layer contains a large amount of a liquid component or the pressure-sensitive adhesive layer is soft or thick.

Under such circumstances that a pressure-sensitive adhesive layer containing a large amount of a liquid component, a soft pressure-sensitive adhesive layer, or a thick pressure-sensitive adhesive layer is employed, a technique for preventing components of the pressure-sensitive adhesive layer of a patch from adhering to the inner surfaces of the package to thereby secure the ease of taking the patch out of the package has become increasingly important in recent years.

SUMMARY OF THE INVENTION

In view of the above, an object of the invention is to provide a patch package structure which enables the patch to be easily taken out of the package.

Such an object of the invention can be unexpectedly accomplished with a compact and simple package prepared by sealing a planar sheet material and a sheet material molded in a given shape, and a given patch. Accordingly, the present invention relates to the followings.

(1) A patch package structure, which comprises:
 a package comprising a first sheet material which is planar and a second sheet material which has been molded, said first and second sheet materials being sealed together in peripheral parts thereof; and
 a patch disposed in the package,
 wherein the patch comprises a backing, a pressure-sensitive adhesive layer laminated on at least one side of the backing, and a release liner which protects a pressure-sensitive adhesive surface of the pressure-sensitive adhesive layer,
 wherein the second sheet material has been molded so as to have a protrudent part in at least a substantially central area thereof, said protrudent part having a planar outer shape larger than a planar outer shape of the release liner and having at least one recessed part,
 wherein d is not smaller than T, in which d is the minimum gap distance between the inner surface of the first sheet material and the inner surface of the second sheet material at the recessed part and T is a thickness of the patch, and
 wherein, at the boundary between the sealed part where the first and second sheet materials are sealed together and an unsealed part, the outer surface of the second sheet material rises at an obtuse angle.

(2) The package structure according to (1) above, wherein the release liner of the patch has a planar outer shape larger than a planar outer shape of the pressure-sensitive adhesive layer.

(3) The package structure according to (1) or (2) above, wherein the patch is disposed in the package in such a way that the release liner faces the inner surface of the first sheet material,
 wherein the release liner has a cut line, and
 wherein the recessed part of the second sheet material is positioned in such a way that the recessed part does not come into contact with a part of the backing which corresponds to the cut line.

(4) The package structure according to any one of (1) to (3) above, wherein the protrudent part has two or more recessed parts.

(5) The package structure according to any one of (1) to (4) above, wherein the pressure-sensitive adhesive layer contains a liquid component.

(6) The package structure according to any one of (1) to (5) above, wherein the patch is an adhesive preparation comprising a pressure-sensitive adhesive layer containing a drug.

The patch package structure of the invention includes a first sheet material which is planar and a second sheet material which has been molded, in which the second sheet material has been molded so that it has a protrudent part in at least a substantially central area thereof, the protrudent part having a outer shape larger than that of the patch and having at least one recessed part therein.

Since the recessed part functions to support the patch, and the inner surface of the protrudent part of the second sheet material is kept apart from peripheral parts of the pressure-sensitive adhesive layer of the patch, the peripheral parts of the pressure-sensitive adhesive layer are less apt to come into contact with the inner surface of the second sheet material. Accordingly, even if the components of the pressure-sensitive adhesive layer protrudes during storage of the patch, the components of the pressure-sensitive adhesive layer are less apt to come into contact with the inner surface of the second sheet material. On the other hand, since the minimum gap distance d between the inner surface of the first sheet material and the inner surface of the second sheet material at the recessed part thereof is not smaller than the thickness of the patch T in the patch package structure of the invention, a load is less apt to be imposed on the patch in the thickness direction therefor. Since the components of the pressure-sensitive adhesive layer are thus inhibited from protruding from peripheral parts of the pressure-sensitive adhesive layer of the patch, the patch is less apt to adhere to the inner surfaces of the package, and therefore, the patch can be easily taken out of the package.

In the case that the patch disposed in the package is one in which the release liner has a planar outer shape larger than that of the pressure-sensitive adhesive layer, even when the patch moves in the package during the storage or transportation of the package structure, the parts which may come into contact with the inner surface of the first sheet material and the inner surface of the second sheet material are limited to peripheral parts of the release liner of the patch, and peripheral parts of the pressure-sensitive adhesive layer come into contact with neither the inner surface of the first sheet material nor the inner surface of the second sheet material. Consequently, even if the components of the pressure-sensitive adhesive layer of the patch protrude from peripheral parts of the pressure-sensitive adhesive layer in this case, the components of the pressure-sensitive adhesive layer are less apt to adhere to the inner surfaces of the package, and therefore, the patch can be very easily taken out of the package.

Furthermore, the outer surface of the second sheet material has a rising part at the boundary between the sealed part of the first sheet material and second sheet material and an unsealed part, and the rising angle thereof is an obtuse angle. Namely, the rising angle is smaller than 180 degrees. Due to this feature coupled with having the recessed part and protrudent part already described above, the package structure of the invention has an advantage that peripheral parts of the pressure-sensitive adhesive layer of the patch are less apt to come into contact with the second sheet material, in comparison with the conventional package structure in a flat bag form obtained by sealing two pieces of planar sheet materials in peripheral parts thereof.

On the other hand, since the rising angle is an obtuse angle, i.e., is larger than 90 degrees and smaller than 180 degrees, the package structure as a whole can be made thin.

Furthermore, since the rising angle is an obtuse angle, there is only a small possibility that the use and molding of a laminated packaging material as the second sheet material might result in a laminate failure such as delamination. Especially in the case of a packaging material including an aluminum foil, the possibility that the aluminum foil itself might crack or otherwise break is small. Consequently, the impermeability to package contents such as a drug, light rays, or gases is less apt to decrease and the quality stability of the patch packaged becomes high.

Moreover, since the rising angle is larger than 90 degrees, when the package is opened by cutting from the sealed part to the unsealed part with scissors, a lot of power is not necessary and the package can be smoothly opened. As a result, the possibility that the patch might be accidentally cut or the scissors might injure the hand is sufficiently low, and the package structure hence has satisfactory handleability.

DESCRIPTION OF THE REFERENCE NUMERALS AND SIGNS 100 patch package structure
101 patch
102 package
103 first sheet material
104 second sheet material
200 patch package structure
201 patch
202 package
203 first sheet material
204 second sheet material
205 sealed part
206 unsealed part
207 backing
208 pressure-sensitive adhesive layer
209 release liner
210 protrudent part
211 recessed part
212 rising angle
301 patch
307 backing
308 pressure-sensitive adhesive layer
309 release liner
400 patch package structure
401 patch
402 package
403 first sheet material
404 second sheet material
405 sealed part
406 unsealed part
407 backing
408 pressure-sensitive adhesive layer
409 release liner
410 protrudent part
411 recessed part
412 rising angle
501 patch
504 second sheet material
507 backing
509 release liner
510 protrudent part
511 recessed part
514 cut line
515 part corresponding to cut line 514
601 patch
604 second sheet material
607 backing
608 pressure-sensitive adhesive layer
609 release liner
611 recessed part
612 recessed part
615 part corresponding to cut line 614
700 patch package structure
701 patch
702 package
704 second sheet material
707 backing
709 release liner
710 protrudent part
711 recessed part
712 recessed part
713 recessed part
714 cut line
1 patch
3 backing
9 slit
10 package
12 blister pack
14 sheet-form cap
16 pinching area
18 central part
22 outer part
24 outer wall
26 flange
28 bottom
8 patch
10 sheet-form packaging material

DETAILED DESCRIPTION OF THE INVENTION

Representative embodiments of the invention will be explained below by reference to drawings. Each drawing is enlarged in the direction perpendicular to the sheet materials (top-and-bottom direction in the drawing) for the purpose of an easy explanation of the concept of the invention. Actual products can be produced in a flatter form.

Figure 1:
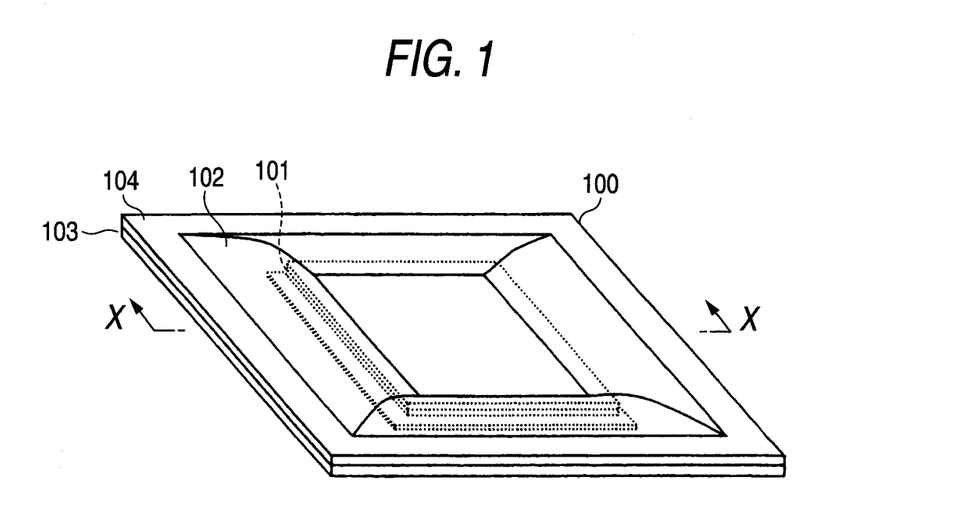
FIG. 1 is a slant view of an embodiment of the patch package structure of the invention.

FIG. 1 is a slant view of a typical embodiment of the patch packing structure of the invention. This patch package structure 100 of the invention includes a patch a package 102 and a patch 101 disposed therein. The package 102 is constituted of a first sheet material 103 which is planar and a second sheet material 104 which has been molded.

Figure 2:
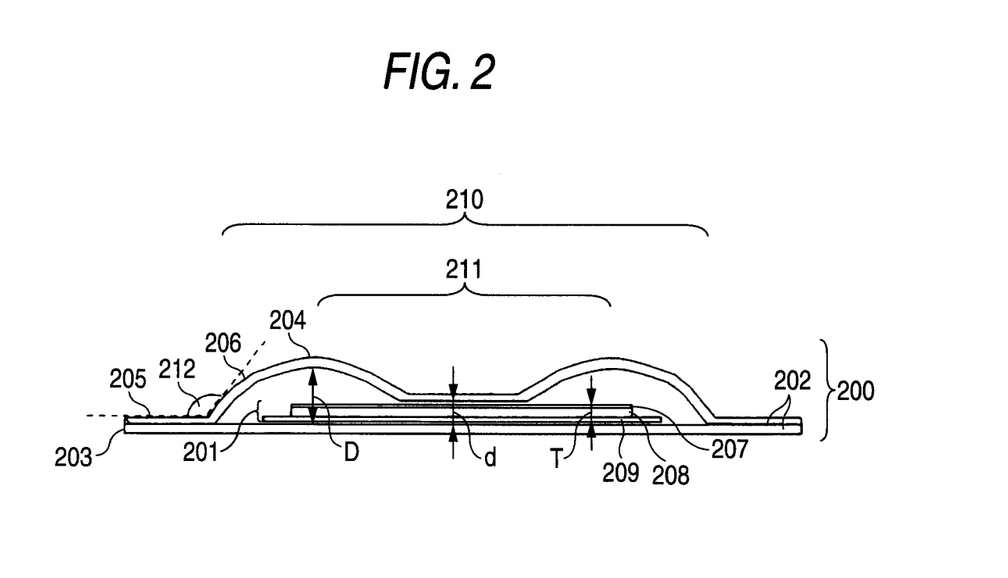
FIG. 2 is a sectional view of the embodiment of the patch package structure of the invention.

FIG. 2 is a sectional view diagrammatically illustrating the cross section of the package structure at the position indicated by X in FIG. 1. This package structure 200 is constituted of a patch 201 and a package 202. The package 202 has a sealed part 205 formed by sealing a first sheet material 203 which is planar and a second sheet material which has been molded in peripheral parts thereof, as well as an unsealed part 206. The patch 201 is disposed in the package 202 constituted of the first sheet material 203 and the second sheet material 204. The package 202 may further contain other substances such as a material for deoxygenation, according to the necessity.

The patch 201 is constituted of a backing 207, a pressure-sensitive adhesive layer 208 formed on at least one side of the backing, and a release liner 209 which protects the pressure-sensitive adhesive surface of the pressure-sensitive adhesive layer. In the invention, the planar outer shape of the release liner may coincide with that of the pressure-sensitive adhesive layer and that of the backing, or may be larger than them. In the embodiment shown in FIG. 2, the planar outer shape of the release liner 209 is larger than that of the pressure-sensitive adhesive layer 208. Namely, the edges of the release liner 209 at least partly have an area or region projecting from the edges of the pressure-sensitive adhesive layer 208. Such an area or region need not surround the whole edges of the pressure-sensitive adhesive layer 208, and the edges of the release liner 209 may partly coincide with the edges of the pressure-sensitive adhesive layer 208.

Since this embodiment has the constitution described above, when the patch 201 moves in the package during the storage or transportation of the package structure 200, those parts in the patch 201 which may come into contact with the inner surface of the first sheet material 203 and the inner surface of the second sheet material 204 are limited to peripheral parts of the release liner 209, and the peripheral parts of the pressure-sensitive adhesive layer 208 of the patch 201 come into contact with neither the inner surface of the first sheet material 203 nor the inner surface of the second sheet material 204.

Figure 3:
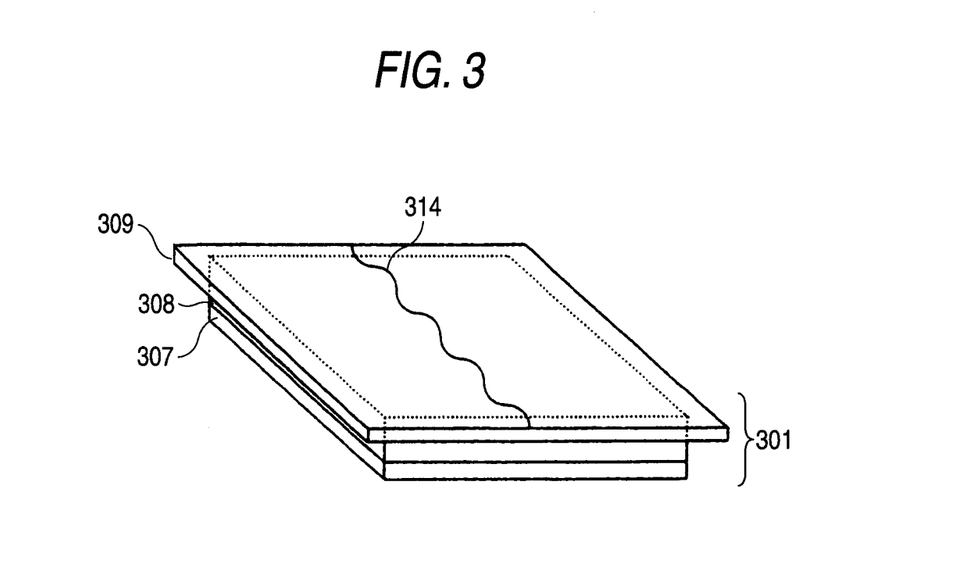
FIG. 3 is a slant view of an example of the patch.

Explanations are then given in reference to FIG. 3. FIG. 3 is a slant view of a patch 301, which corresponds to the patch 101 shown in FIG. 1. This patch 301 includes a backing 307, a pressure-sensitive adhesive layer 308 formed on one side of the backing 307, and a release liner 309 attached to the surface of the pressure-sensitive adhesive layer 308 in order to protect the pressure-sensitive adhesive layer 308. The planar outer shape of the release liner 309 is larger than that of the pressure-sensitive adhesive layer 308. Unlike FIG. 1, FIG. 3 illustrates the patch, with the release liner 309 above and the backing 307 below for convenience.

In the embodiment shown in FIG. 3, the release liner 309 has a wavy cut line 314 so that the user can easily peel off the release liner 309 from the pressure-sensitive adhesive layer 308 at the time of application to the skin. In preparation for application, when the user slightly bends the patch 302 so as to form a ridge along the cut line 314, areas suitable for pinching for peeling off the release liner 309 are easily obtained. It is therefore preferred to form such a cut line 314 in the release liner 309. The planar shape of the cut line may be a continuous line or a broken line, and the planar shape thereof is not limited to a wavy line and the examples thereof include a substantially straight line and a zigzag line. A wavy line or a zigzag line is preferred from the standpoint of easily obtaining pinching areas for peeling off the release liner. The cut line need not be completely continuous, i.e., may be separated, and the cut line may have uncut areas so long as the uncut areas can be broken with fingers.

With reference to FIG. 2 again, the second sheet material 204 has a protrudent part 210. Attention is directed to one end of the package structure in the cross section of the package structure shown in FIG. 2. The first sheet material 203 begins at one end, extends substantially linearly, and ends at the other end. The second sheet material 204 begins at or near one end, forms a cross section having a given shape, and ends at or near the other end.

With respect to the given shape in the embodiment shown in FIG. 2, the second sheet material 204 extends from one end to the other end. In this embodiment, the second sheet material 204 begins at one end, extends substantially linearly from this end almost parallel with the first sheet material 203 to form a sealed part 205, and reaches a rising part. The term "rising part" herein means a part where the second sheet material 204 shifts from the sealed part 205 to the unsealed part 206. At the rising part, the second sheet material 204 has a given rising angle 212.

After passing through this rising part, the second sheet material 204 begins to get away from the first sheet material 203 and begins to approach again the first sheet material 203 at a first part. At this first part, the inner surface of the first sheet material 203 and the inner surface of the second sheet material 204 provide a first distance. Subsequently, the second sheet material 204 which has begun to approach the first sheet material 203 begins to get away again from the first sheet material 203 at a second part. At this second part, the inner surface of the first sheet material 203 and the inner surface of the second sheet material 204 provide a second distance. Subsequently, the second sheet material 204 which has begun to get away from the first sheet material 203 begins to approach again the first sheet material 203 at a third part. At this third part, the inner surface of the first sheet material 203 and the inner surface of the second sheet material 204 provides a third distance.

Subsequently, the second sheet material 204 which has begun to approach the first sheet material 203 reaches another rising part, extends again substantially linearly and almost parallel with the first sheet material 203 to form another sealed part, and ends at the other end.

In the embodiment shown in FIG. 2, the larger of the first distance and the third distance indicates a maximum gap distance D between the inner surface of the first sheet material 203 and the inner surface of the second sheet material 204. The first distance may be the same as third distance; in this case, the maximum gap distance D is equal to the first distance and also to the third distance. On the other hand, the second distance indicates a minimum gap distance d between the inner surface of the first sheet material 203 and the inner surface of the second sheet material 204.

In the invention, the region ranging from one rising part to another rising part is referred to as a protrudent part, which is denoted by 210 in FIG. 2. On the other hand, the region ranging from the part providing the first distance to the part providing the third distance is referred to as a recessed part, which is denoted by 211 in FIG. 2. In this embodiment, the recessed part 211 is disposed in a substantially central part of the protrudent part 210 from the standpoints of ease of molding, shape stability, and the like.

There are cases where the protrudent part 210 is constituted of flat surfaces as in embodiments which will be described later. However, package structures in which the protrudent part 210 includes curved surfaces as in the embodiment shown in FIG. 2 have a high thickness-direction strength. Furthermore, when the protrudent part 210 is constituted of curved surfaces, molding is easy. Additionally, since the package structure can have a relatively small internal volume, the stability of the patch becomes high.

In the embodiment shown in FIG. 2, the bottom of the recessed part 211 is substantially flat. Although such a bottom may be either substantially flat or curved in the invention, it is preferred that the bottom be substantially flat from the standpoint of reducing the load per unit area to be imposed on the region which may come into contact with the patch.

Since this recessed part 211 functions so as to support the patch 201, and the inner surface of the protrudent part 210 of the second sheet material 204 is kept apart from peripheral parts of the pressure-sensitive adhesive layer 208 of the patch 201, the peripheral parts of the pressure-sensitive adhesive layer are less apt to come into contact with the inner surface of the second sheet material.

Furthermore, in the recessed part 211 of the second sheet material 204 in FIG. 2, the minimum gap distance d between the inner surface of the first sheet material 203 and the inner surface of the second sheet material 204 is not smaller than the thickness T of the patch 201, and is preferably larger than T. Accordingly, a load is less apt to be imposed on the patch 201 in the thickness direction therefor, and therefore, components of the pressure-sensitive adhesive layer are inhibited from protruding from peripheral parts of the pressure-sensitive adhesive layer 208 of the patch 201. This is effective especially in the patch 302 in which the release liner 309 has a cut line 314 as in the case explained above by reference to FIG. 3, because the components of the pressure-sensitive adhesive layer are inhibited from protruding from the cut line 314 upon reception of such a load. In specific examples, T is 0.2-0.3 mm and d is 0.5-2.0 mm.

As shown in FIG. 2, the second sheet material 204 has the rising parts. The rising angle 212 in each rising part is an obtuse angle, i.e., larger than 90 degrees and smaller than 180 degrees.

In a case where the rising angle 212 is 90 degrees or smaller, this package structure as a whole becomes thick. Furthermore, such a package structure has a drawback that when it is opened by cutting from the sealed part 205 to the unsealed part 206 with scissors, a lot of power is necessary and the package structure cannot be smoothly opened. In a case where the rising angle 212 is 180 degrees, this means that the package structure has no rising part, and therefore, there is a possibility that peripheral parts of the pressure-sensitive adhesive layer 208 of the patch might come into contact with the second sheet material 204.

The rising angle 212 herein means the angle formed, at the boundary between the sealed part 205 where the first and second sheet materials are sealed together and the unsealed part 206, by the outer surface of the second sheet material 204 in the sealed part 205 and the outer surface of the second sheet material 204 in the unsealed part 206. These outer surfaces may be flat or curved. In the case where the outer surface of the second sheet material 204 in the unsealed part 206 is curved as shown in FIG. 2, the rising angle 212 means the angle formed by a flat plane circumscribed about the unsealed part 206 at the boundary and the outer surface of the second sheet material 204 in the sealed part 205. This can be applied in the case where the sealed part 205 is curved.

The rising angle 212 is preferably 95-175 degrees, more preferably 100-170 degrees, even more preferably 110-165 degrees, and most preferably 115-160 degrees. By employing such a rising angle 212, the package structure 200 as a whole can be made thin and such a thin package structure is advantageous from the standpoints of the cost of package structure production and the cost of handling of packaged products such as transportation thereof. Furthermore, such a thin package structure can be easily opened with scissors or the like.

The maximum gap distance D between the package inner surface of the protrudent part 210 of the second sheet material 204 and the package inner surface of the first sheet material 203, as shown in FIG. 2, is not particularly limited. However, it is preferred that D be smaller than 2.6 d in order to make the package structure 200 as a whole thin to thereby reduce the volume thereof. Symbol d is the minimum gap distance between the inner surface of the first sheet material 203 and the inner surface of the second sheet material 204 in the recessed part of the second sheet material 204. D is more preferably smaller than 2.3 d, even more preferably smaller than 2.0 d, especially preferably smaller than 1.7 d, and most preferably smaller than 1.5 d. Incidentally, D is inevitably larger than d because the recessed part 211 is located in the protrudent part 210.

The planar outer shape of the patch, that of the package structure, and that of the protrudent part are not particularly limited. Examples thereof include substantially polygonal shapes, such as substantially rectangular shapes, substantially elliptic shapes, and substantially circular shapes. From the standpoint of diminishing defects in the sheet materials, etc., substantially rectangular shapes such as that shown in FIG. 1 are preferred. From the standpoint of packaging efficiency, it is preferred that the planar outer shapes thereof should be substantially similar to each other.

In a specific example of the embodiment shown in FIG. 2, the backing 207 and pressure-sensitive adhesive layer 208 of the patch 201 each have a substantially rectangular planar outer shape in which one side has a length of 20-100 mm and another side has a length of 20-100 mm, and the release liner 209 has a substantially rectangular planar outer shape in which one side has a length of 22-104 mm and another side has a length of 22-104 mm. The release liner 209 of this example hence has a strip-shaped projecting peripheral area having a width of 1-2 mm.

In order to have peripheral parts of the pressure-sensitive adhesive layer of the patch to be sufficiently apart from the inner surface of the second sheet material, the planar outer shape of the protrudent part is preferably larger than that of the release liner of the patch. From the same standpoint, the planar outer shape of the bottom of the recessed part is preferably smaller than that of the pressure-sensitive adhesive layer.

In a specific example of the embodiment shown in FIG. 2, the protrudent part 210 has a substantially rectangular planar outer shape in which one side has a length of 30-110 mm and another side has a length of 30-110 mm; the recessed part 211 has a substantially rectangular planar outer shape in which one side has a length of 20-100 mm and another side has a length of 20-100 mm; and the bottom of the recessed part 211 has a substantially rectangular outer shape in which one side has a length of 10-90 mm and another side has a length of 10-90 mm. By employing such a shape, the peripheral parts of the pressure-sensitive adhesive layer 208 can be sufficiently apart from the inner surface of the second sheet material 204, whereby the components of the pressure-sensitive adhesive layer are less apt to adhere to the inner surfaces of the package 202.

The first sheet material and second sheet material in the patch package structure of the invention described above are not particularly limited so long as both materials can be sealed together for forming the package. Heat-sealable sheet materials are preferred from the standpoint of ease of production. Examples of such packaging materials include films of resins such as polyolefins including polyethylene and polypropylene, polyesters including poly(ethylene terephthalate), and other resins including poly(vinyl chloride) and polyacrylonitrile, metal films such as aluminum foils, materials obtained by vapor-depositing aluminum on these films, and laminated films obtained by laminating two or more thereof.

From the standpoints of impermeability to package contents such as a drug and heat sealability, a polyacrylonitrile film or the like is preferred for use as such a packaging material. From the standpoint of non-adsorptive property of package contents such as a drug, it is preferred to employ a polyester, especially poly(ethylene terephthalate) or the like. From the standpoint of impermeability to package contents, light rays or gases, more preferred packaging materials are those resin films which have undergone aluminum vapor deposition and laminated films obtained by laminating an aluminum foil to those resin films. More preferred from the standpoint of combining those properties are laminated films obtained by laminating polyesters, in particular poly(ethylene terephthalate) and a polyacrylonitrile film. Most preferred is a laminated film obtained by laminating polyesters, in particular poly(ethylene terephthalate), an aluminum foil or vapor-deposited aluminum layer, and a polyacrylonitrile film. From the standpoint of the storage stability of package contents such as a drug, a laminated film obtained by laminating a water-impermeable layer to the outer side of a hygroscopic layer containing a drying agent and a water-permeable layer respectively is also preferred.

Materials and constitutions of the first sheet material and the second sheet material may be the same or different. The first sheet material is preferably made of a flexible material because such sheet material can be easily sealed with the second sheet material to thereby facilitate production. The second sheet material is preferably made of a rigid material because it is molded into a given shape.

The invention can be especially advantageously practiced when a laminated film is employed, in particular when the second sheet material includes an aluminum foil or vapor-deposited aluminum layer. This is because due to the given rising angle, the laminate during molding is less apt to break or to undergo the breakage of the aluminum foil or vapor-deposited aluminum layer.

The thickness of the first sheet material is not particularly limited. However, it is preferably 10-200 μm, and more preferably 20-100 μm, from the standpoints of production efficiency and impermeability to components to be packaged in the package structure.

The thickness of the second sheet material is not particularly limited. It is, however, preferred that the second sheet material have some degree of stiffness because of the necessity of molding into the given shape. From this standpoint, the thickness thereof is preferably 50-300 μm, and more preferably 50-200 μm.

Methods for molding the second sheet material into the given shape are not limited. Examples thereof include vacuum/pressure forming, injection molding, and press molding. From the standpoints of suitability for cost reduction, degree of freedom of shapes, material selection, etc., vacuum forming, pressure forming, and the like are preferred.

As described above, the patch included in the patch package structure of the invention is constituted of a backing, a pressure-sensitive adhesive layer formed on at least one side of the backing, and a release liner which protects the pressure-sensitive adhesive surface of the pressure-sensitive adhesive layer. The outer shape of the release liner is not particularly limited so long as it is larger than the outer shape of the pressure-sensitive adhesive layer.

The patch may be an adhesive preparation in which the pressure-sensitive adhesive layer contains a drug. The drug herein is not particularly limited. Preferred is a drug which can be administered to a mammal such as a human being through the skin, i.e., which is percutaneously absorbable. Examples of such drugs include systemic anesthetics, hypnotic agents, antiepileptics, antipyretic/analgesic/antiphlogistic agents, antidizzying agents, psychoneurotics, local anesthetics, skeletal muscle relaxants, agents for autonomous nerve, antispasmodics, anti-Parkinsonian agents, antihistamines, cardiotonics, antiarrhythmics, diuretics, antihypertensives, vasoconstrictors, coronary vasodilators, peripheral vasodilators, antiarteriosclerotic agents, agents for circulatory organs, respiration facilitators, antitussive/expectorant agents, hormone drugs, external-use preparations for purulent diseases, analgesic/antipruritic/astringent/antiphlogistic agents, agents for parasitic skin diseases, hemostats, antipodagrics, agents for diabetes, antineoplastics, antibiotics, chemotherapeutics, narcotics, and smoking renunciation aids.

The content of the percutaneously absorbable drug is not particularly limited so long as it sufficiently produces the effect thereof and does not impair the adhesiveness of the pressure-sensitive adhesive. However, the content thereof in the pressure-sensitive adhesive is preferably 0.1-60% by weight, and more preferably 0.5-40% by weight. In the case where the content thereof is lower than 0.1% by weight, there is a possibility that the remedial effect might be insufficient. In the case where the content thereof is higher than 60% by weight, there is a possibility that skin irritation might occur and such a large drug amount might be economically disadvantageous.

The pressure-sensitive adhesive is not particularly limited. Examples thereof include acrylic pressure-sensitive adhesives containing an acrylic polymer; rubber-based pressure-sensitive adhesives such as styrene/diene/styrene block copolymers (e.g., styrene/isoprene/styrene block copolymers and styrene/butadiene/styrene block copolymers), polyisoprene, polyisobutylene, and polybutadiene; silicone type pressure-sensitive adhesives such as silicone rubbers, dimethylsiloxane-based polymers, and diphenylsiloxane-based polymers; vinyl ether type pressure-sensitive adhesives such as poly(vinyl methyl ether), poly(vinyl ethyl ether), and poly(vinyl isobutyl ether); vinyl ester type pressure-sensitive adhesives such as vinyl acetate/ethylene copolymers; and polyester type pressure-sensitive adhesives produced from a carboxylic acid component such as dimethyl terephthalate, dimethyl isophthalate, or dimethyl phthalate, and a polyhydric alcohol component such as ethylene glycol.

Acrylic pressure-sensitive adhesives or rubber-based pressure-sensitive adhesives are preferred among such pressure-sensitive adhesives because acrylic or rubber-based pressure-sensitive adhesives give a pressure-sensitive adhesive layer which is capable of holding a liquid component therein and hence can give a soft feeling during wear on the skin. In particular, acrylic pressure-sensitive adhesives are preferred because they can be easily crosslinked and give a pressure-sensitive adhesive layer capable of holding a large amount of a liquid component therein.

Examples of such acrylic pressure-sensitive adhesives include acrylic ester type pressure-sensitive adhesives containing as the main component a polymer comprising monomer units derived from one or more $C_{2-18}$ alkyl esters of (meth)acrylic acid. Examples of those rubber-based pressure-sensitive adhesives include rubber-based pressure-sensitive adhesives containing as the main component at least one member selected from polyisobutylene, polyisoprene, and styrene/diene/styrene copolymers.

The liquid component is not particularly limited. From the standpoint of compatibility with the pressure-sensitive adhesive layer, organic liquid components are preferred. Although the organic liquid components are not particularly limited, ones having the effect of accelerating percutaneous absorption are preferred. Examples of such organic liquid components include glycols such as ethylene glycol, diethylene glycol, propylene glycol, triethylene glycol, polyethylene glycol, and polypropylene glycol; fats and oils such as olive oil, caster oil, squalane, and lanolin; hydrocarbons such as liquid paraffin; various surfactants; ethoxy stearyl alcohol; glycerol monoesters such as oleic acid monoglyceride, caprylic acid monoglyceride, and lauric acid monoglyceride, glycerol diesters, glycerol triesters, and mixtures thereof; alkyl esters of fatty acids, such as ethyl laurate, isopropyl myristate, isotridecyl myristate, octyl palmitate, isopropyl palmitate, ethyl oleate, and diisopropyl adipate; higher fatty acids such as oleic acid and caprylic acid; and other compounds including N-methylpyrrolidone and 1,3-butanediol.

In the case that a liquid component is contained in the pressure-sensitive adhesive layer, there is a possibility that components of the pressure-sensitive adhesive layer might protrude, during storage of the patch, from peripheral parts of the pressure-sensitive adhesive layer or from the cut line optionally formed in the release liner. The invention is advantageously practiced especially in such cases. From this standpoint, the content of the liquid component in the pressure-sensitive adhesive layer is preferably 5-70% by weight, more preferably 10-65% by weight, and most preferably 15-60% by weight.

When the pressure-sensitive adhesive layer is relatively thick, the thickness of this pressure-sensitive adhesive layer is preferably 20-300 μm, more preferably 30-250 μm, and most preferably 50-200 μm.

Preferred alternative embodiments of the invention are explained below by reference to other drawings. In these embodiments, the constitutions are the same as those of the embodiment shown in FIGS. 1 and 2, unless otherwise indicated.

Figure 4:
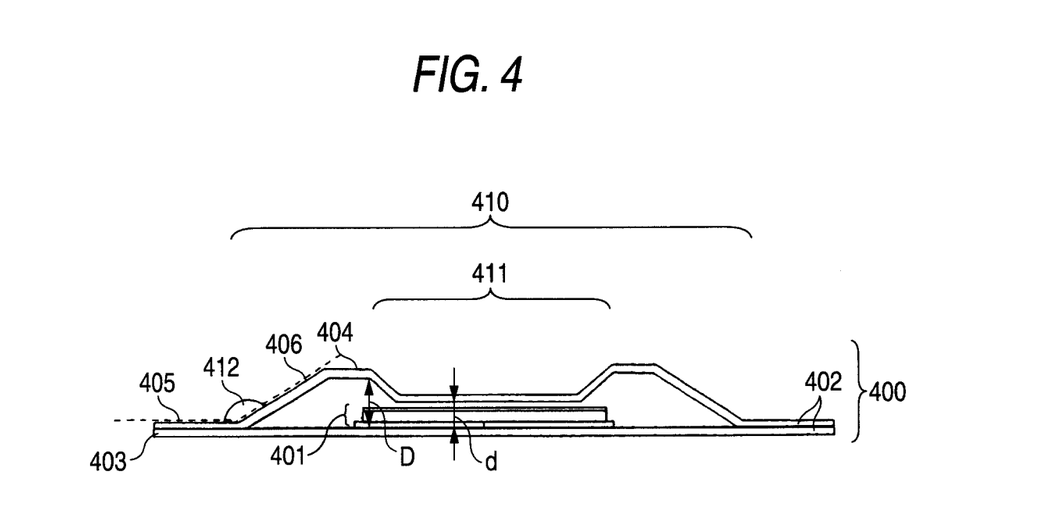
FIG. 4 is a sectional view of another embodiment of the patch package structure of the invention.

FIG. 4 shows an embodiment in which the second sheet material has a shape having substantially flat surfaces. In this embodiment, the second sheet material 404 has a region in which it is almost linear and substantially parallel with the inner surface of the first sheet material 403, in each of a first part where the second sheet material 404 has a first distance from the inner surface of the first sheet material 403 and a third part where the second sheet material 404 has a third distance from the inner surface of the first sheet material 403, as defined above by reference to FIG. 2. In this embodiment, the region ranging from the point in the part where the inner surface of the second sheet material 404 provides the first distance from the inner surface of the first sheet material 403 which is closest to the center of the package structure 400 to the point in the part where the inner surface of the second sheet material 404 provides the third distance from the inner surface of the first sheet material 403 which is closest to the center of the package structure 400 is referred to as a recessed part, which is denoted by 411 in FIG. 4.

As shown in the package-structure sectional view in FIG. 4, the second sheet material 404 in this embodiment passes through a rising part and then extends substantially linearly to the first part. In this package structure embodiment, the outer surface of the second sheet material 404 at each boundary between the sealed part 405 and the unsealed part 406 in FIG. 4 may have a large rising angle 412 in comparison with the package structure of the type shown in FIG. 2 which has the same volume. Consequently, this package structure can be smoothly opened with scissors.

Figure 5:
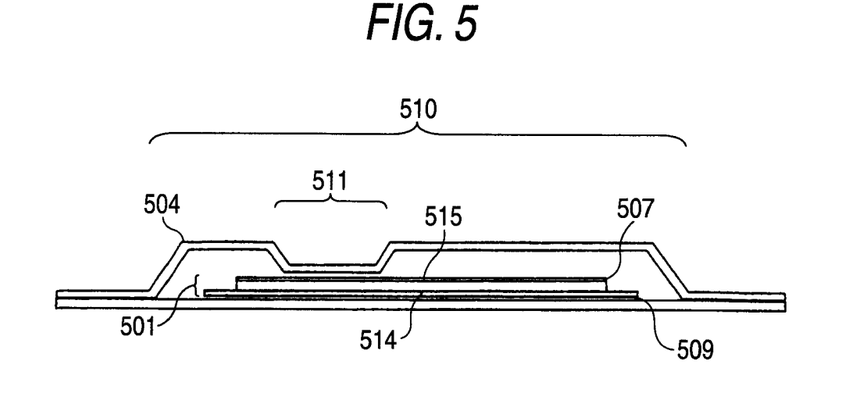
FIG. 5 is a sectional view of still another embodiment of the patch package structure of the invention.

FIG. 5 is a diagrammatic sectional view of an embodiment in which the protrudent part 510 of the second sheet material 504 has a recessed part 511 in such a position that the recessed part 511 does not come into contact with the backing 507 of that part 515 which corresponds to the cut line 514 of the release liner 509. Since the recessed part 511 is disposed in such a position, a load is inhibited from being imposed in the thickness direction for the patch 501 on the part 515 corresponding to the cut line 514 formed in the release liner 509 of the patch 501 even when the second sheet material 504 deforms slightly. Consequently, components of the pressure-sensitive adhesive layer are inhibited from protruding from the cut line 514.

Figure 6:
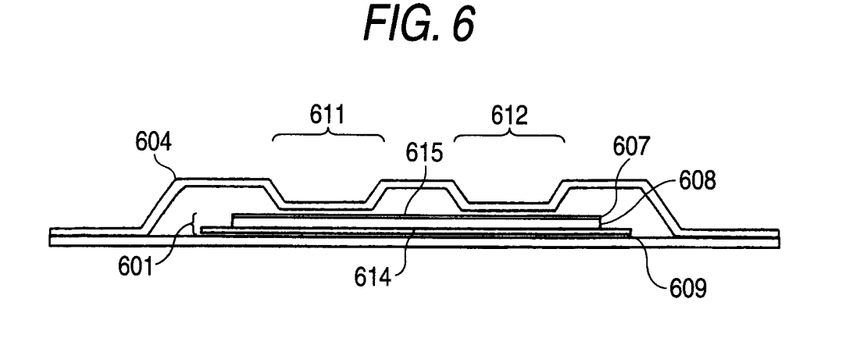
FIG. 6 is a sectional view of a further embodiment of the patch package structure of the invention.

FIG. 6 is a diagrammatic sectional view of an embodiment in which the protrudent part of the second sheet material 604 has two or more recessed parts, i.e., a recessed part 611 and a recessed part 612 in this case. By thus forming two or more recessed parts, the load to be imposed on the patch 601 in the thickness direction therefor can be dispersed to thereby reduce such load per unit area. Consequently, components of the pressure-sensitive adhesive layer can be inhibited from protruding from peripheral and other parts of the pressure-sensitive adhesive layer 608. Furthermore, as shown in FIG. 6, the recessed part 611 and the recessed part 612 have been formed in such positions that they do not come into contact with that part 615 of the backing 607 of the patch 601 which corresponds to the cut line 614 of the release liner 609. Because of this, a load is inhibited from being imposed in the thickness direction for the patch 601 on the part 615 corresponding to the cut line 614 formed in the release liner 609 of the patch 601. Consequently, components of the pressure-sensitive adhesive layer are inhibited from protruding from the cut line 614.

Figure 7:
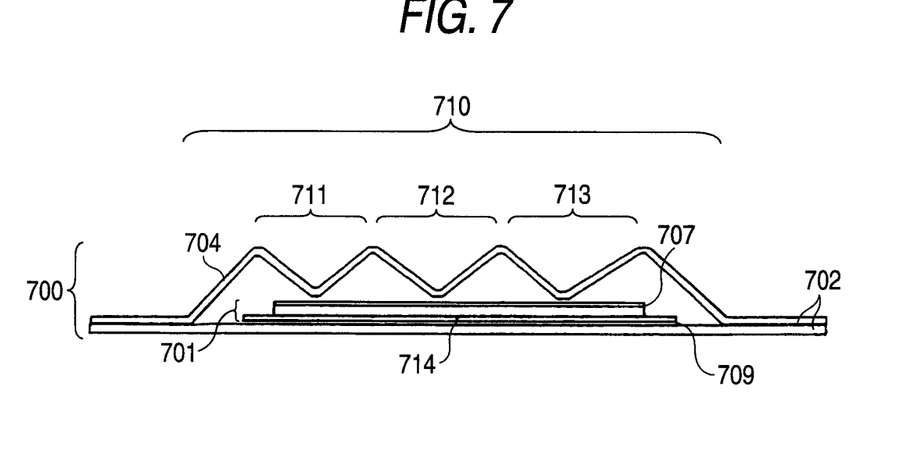
FIG. 7 is a sectional view of still a further embodiment of the patch package structure of the invention.

FIG. 7 is a diagrammatic sectional view of an embodiment in which the protrudent part 710 of the second sheet material 704 has three recessed parts 711, 712, and 713. By forming a lot of recessed parts as in this embodiment, the outer shape per recessed part can be smaller. Consequently, the package 702 can have enhanced rigidity.

While the present invention has been described in detail and with reference to specific embodiments thereof, it will be apparent to one skilled in the art that various changes and modifications can be made therein without departing from the scope thereof.

This application is based on Japanese patent application No. 2007-003313 filed Jan. 11, 2007, the entire contents thereof being hereby incorporated by reference.

Further, all references cited herein are incorporated in their entireties.

What is claimed is:

1. A patch package structure, which comprises:
   a package comprising a first sheet material which is planar and a second sheet material which has been molded, said first and second sheet materials being sealed together in peripheral parts thereof; and
   a patch disposed in the package,
   wherein the patch comprises a backing, a pressure-sensitive adhesive layer laminated on at least one side of the backing, and a release liner which protects a pressure-sensitive adhesive surface of the pressure-sensitive adhesive layer,
   wherein the second sheet material has been molded so as to have a protrudent part in at least a substantially central area thereof, said protrudent part having a planar outer shape larger than a planar outer shape of the release liner and having at least one recessed part, wherein d is equal to T, in which d is the minimum gap distance between the inner surface of the first sheet material and the inner surface of the second sheet material at the recessed part and T is a thickness of the patch, so as to reduce vertical movement of the patch inside the package, wherein, at the boundary between the sealed part where the first and second sheet materials are sealed together and an unsealed part, the outer surface of the second sheet material rises at an obtuse angle, wherein a maximum gap distance D between a package inner surface of the protrudent part of the second sheet material and the package inner surface of the first sheet material is larger than d and is smaller than 2.3×d, and wherein the obtuse angle is in the range of 95 to 175 degrees.

2. The package structure according to claim 1, wherein the release liner of the patch has a planar outer shape larger than a planar outer shape of the pressure-sensitive adhesive layer.

3. The package structure according to claim 1, wherein the patch is disposed in the package in such a way that the release liner faces the inner surface of the first sheet material, wherein the release liner has a cut line, and wherein the recessed part of the second sheet material is positioned in such a way that the recessed part does not come into contact with a part of the backing which corresponds to the cut line.

4. The package structure according to claim 1, wherein the protrudent part has two or more recessed parts.

5. The package structure according to claim 1, wherein the pressure-sensitive adhesive layer contains a liquid component.

6. The package structure according to claim 1, wherein the patch is an adhesive preparation comprising a pressure-sensitive adhesive layer containing a drug.

7. The package structure according to claim 1, wherein the unsealed part is formed on a curved part which has a curved surface.

* * * * *